US00PP16762P3

(12) United States Plant Patent
Lintott

(10) Patent No.: US PP16,762 P3
(45) Date of Patent: Jul. 4, 2006

(54) ***CHRYSANTHEMUM* PLANT NAMED 'STARSTRUCK PINK'**

(50) Latin Name: *Chrysanthemum morifolium*
Varietal Denomination: Starstruck Pink

(75) Inventor: Keith G. Lintott, Bognor Regis (GB)

(73) Assignee: Cleangro, Ltd, Chichester (GB)

( * ) Notice: Subject to any disclaimer, the term of this patent is extended or adjusted under 35 U.S.C. 154(b) by 41 days.

(21) Appl. No.: 11/055,172

(22) Filed: Feb. 9, 2005

(65) Prior Publication Data

US 2005/0177908 P1 Aug. 11, 2005

Related U.S. Application Data

(60) Provisional application No. 60/543,818, filed on Feb. 10, 2004.

(51) Int. Cl.
*A01H 5/00* (2006.01)

(52) U.S. Cl. ..... Plt./297

(58) Field of Classification Search ..... Plt./297
See application file for complete search history.

(56) References Cited

PUBLICATIONS

Royal Van Zanten Gardenmum Catalog 2002 listing the variety 'Dove'. See, e.g., pp. 5 (photograph) and 9.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Starstruck Pink ' having a domed capitulum of medium sized deep pink single type flowers and a round shape.

1 Drawing Sheet

Latin name of the genus and species: Botanical classification: *Chrysanthemum morifolium.*

Variety denomination: The new *Chrysanthemum* variety denomination is 'Starstruck Pink.'

BACKGROUND OF THE INVENTION

The present invention comprises a new and distinct cultivar of *Chrysanthemum* botanically known as *Chrysanthemum morifolium,* and referred to by the variety name 'Starstruck Pink.'

'Starstruck Pink,' identified as 31116-0, originated from a cross made in a controlled breeding program in West Sussex, United Kingdom. The female parent of the new *Chrysanthemum* variety is the variety known as 'Chicane.' The male parent of the new *Chrysanthemum* variety is an undistributed, unpatented seedling identified as '98.027-67.' The new *Chrysanthemum* variety 'Starstruck Pink' has been asexually reproduced by vegetative cuttings in Chichester, West Sussex, United Kingdom and the distinguishing characteristics are retained throughout successive generations of asexual reproduction.

BRIEF SUMMARY OF THE INVENTION

'Starstruck Pink' is a garden type of *Chrysanthemum* plant variety having a domed-round canopy of pink single type flowers.

Comparison with Female Parent

Plants of the new *Chrysanthemum* variety 'Starstruck Pink' are dissimilar to the parent variety 'Chicane' in plant habit and growth rate. In side-by-side comparisons in Chichester, West Sussex, United Kingdom, under commercial practice, plants of the new *Chrysanthemum* variety 'Starstruck Pink' differed from plants of the parent variety 'Chicane' in the following characteristics.

1. The new *Chrysanthemum* variety 'Starstruck Pink' produces deep pink single type flowers whereas the parent variety 'Chicane' produces light pink single type flowers.

2. Plants of the new *Chrysanthemum* variety 'Starstruck Pink' have smaller and shorter inflorescence than plants of the parent variety 'Chicane.'

3. The new *Chrysanthemum* variety 'Starstruck Pink' is less vigorous than the parent variety 'Chicane.'

Comparison with Male Parent

Plants of the new *Chrysanthemum* variety 'Starstruck Pink' are dissimilar to the parent variety '98.027-67' in plant habit and growth rate. In side-by-side comparisons in Chichester, West Sussex, United Kingdom, under commercial practice, plants of the new *Chrysanthemum* variety 'Starstruck Pink' differed from plants of the parent variety '98.027-67' in the following characteristics.

1. The new *Chrysanthemum* variety 'Starstruck Pink' produces deep pink single type flowers whereas the parent variety '98.027-67' produces white single type flowers.
2. Plants of the new *Chrysanthemum* variety 'Starstruck Pink' have smaller and shorter inflorescence than plants of the parent variety '98.027-67.'
3. Plants of the new *Chrysanthemum* variety 'Starstruck Pink' have a natural season response of about 9 weeks whereas plants of the parent variety '98.027-67' have a natural season response time of near 10 weeks.

Comparison with the Variety 'Dove'

Plants of the new *Chrysanthemum* variety 'Starstruck Pink' are similar to the unpatented variety 'Dove' in plant habit and growth rate. However, in side-by-side comparisons in Chichester, West Sussex, United Kingdom, under commercial practice, plants of the new *Chrysanthemum* variety 'Starstruck Pink' differed from plants of the variety 'Dove' in the following characteristics:

1. The new *Chrysanthemum* variety 'Starstruck Pink' produces deep pink, single type flowers whereas the variety 'Dove' produces smaller deep pink single type flowers.
2. Plants of the new *Chrysanthemum* variety 'Starstruck Pink' have a more uniform flowering response than plants of the variety 'Dove.'

BRIEF DESCRIPTION OF ILLUSTRATION

Typical specimens of the plant and flowers for the new *Chrysanthemum* variety 'Starstruck Pink' are shown in the accompanying digital photograph. The colors shown are as true as possible within the usual limits of this kind of illustration.

FIG. 1 is a whole plant view of the new *Chrysanthemum* variety 'Starstruck Pink' grown in a pot. The plant shown in the illustration is 63 days from the commencement of planting outdoors in mid-June.

DETAILED BOTANICAL DESCRIPTION

The following description of the new *Chrysanthemum* variety 'Starstruck Pink' is of plants grown outside, natural season, in Chichester, West Sussex, United Kingdom in the month of June. The variety has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 60° F. to 75° F. during the day under natural light conditions. The plants were grown outdoors in mid-June in 4 liter pots using loamless compost. No growth retardants were used. To produce a commercial product the plants may be pinched once with the center bud removed. The typical container size for commercial growth is 4 liters (8"). It has been observed that the shelf life of the new variety is about 25 days with a response time of about 9 weeks natural season. The new variety is suitable for growth in a temperature range of 50° F. to 75° F.

The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed-Round.
Height: 45 cm–55 cm.
Width: 40 cm–55 cm.
Stem:
- *Length.*—6 cm–9 cm.
- *Diameter.*—0.5 cm–0.8 cm.
- *Texture.*—Rough.
- *Color.*—Near 137A.

Branching characteristics: Free branching/Spreading.
Lateral branches:
- *Length.*—14 cm–18 cm.
- *Diameter.*—0.4 cm–0.6 cm.
- *Texture.*—Slightly pubescent.

Number of breaks from pinch: 7–12.
Response time: 9 weeks natural season.
Vigor: Medium.
Shelf life: 25 days.
Disease (susceptibility/resistance observed): None observed to date.
Pest (susceptibility/resistance observed): None observed to date.
Drought and temperature (susceptibility/resistance observed): None observed to date.
Growth retardant type and treatment: No treatment necessary. The plants were grown for 9 weeks in natural season conditions.
Propagation:
- *Type.*—Vegetative Propagation via Stem Cuttings.
- *Time to rooting.*—12 days with soil temperatures of 70° F.
- *Rooting habit.*—Fine and Fibrous.

Foliage

Number of leaves per lateral branch: 8–12.
Compound or single: Single.
Arrangement of Leaves: Alternate.
- *Shape of leaf.*—Typically 5 lobed Ovate.
- *Size of leaf.*—Width: 2.5 cm–3.5 cm. Length: 3.5 cm–5 cm.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Smooth Slightly pubescent. Bottom: Slightly pubescent.

Petiole:
- *Color.*—Near 138B.
- *Length.*—0.7 cm–1.1 cm.
- *Diameter.*—0.3 cm–0.5 cm.

Venation: Net. Prominent mid vein at underside.
- *Color.*—Upper side: near 138C. Under side: near 138C.

Color:
- *Mature leaf, upper side.*—Near 137B under side: near 138A.
- *Young leaf, upper side.*—Near 137B; under side: near 138A.

Flower

Flower appearance: Matte.
Flower type: Single.
Flower form: Flat.
Flower shape: Round.
Flowering habit: Cyme.
Number of blossoms per branch: 9–15.
Typical and observed flowering season: August and September natural season.
Inflorescence form: Corymibiform.
- *Depth of fully expanded blossoms.*—0.7 cm–0.8 cm.
- *Diameter of fully expanded blossoms.*—3.5 cm–5.0 cm.

Phyllaries:
- *Number.*—23–25.
- *Color.*—Near 138A.
- *Length.*—0.2 cm–0.5 cm.
- *Width.*—0.1 cm–0.3 cm.
- *Texture/appearance.*—Slightly shiny and pubescent.

Peduncle: Peduncle length is shortest at the terminal flower and progressively longer down the stem; longest length is on average 14 cm, shortest length is on average 10 cm.
- *Length.*—9 cm–15 cm.

*Diameter.*—0.5 cm–0.7 cm.
*Color.*—Near 138B.
*Surface.*—Slightly Pubescent.
*Habit.*—Very slightly curving.
*Strength.*—Medium.

Pedicel:
*Length.*—Terminal: 7 cm–9 cm; lateral 11 cm–13 cm.
*Diameter.*—0.3 cm–0.5 cm.
*Color.*—Near 137A.
*Surface.*—Slightly pubescent.
*Habit.*—Slightly curving.
*Strength.*—Medium/strong.

Ray florets:
*Form/shape.*—Straight.
*Texture/appearance.*—Matte.
*Number per flower.*—30–35.
*Length.*—1 cm–2 cm; Width: 0.2 cm–0.4 cm.
*Apex.*—Round.
*Base.*—Tubular.
*Margin.*—Entire.

Disc florets:
*Form/shape.*—Cylindrical.
*Texture/appearance.*—Matte.
*Number per flower.*—130–150.
*Length.*—0.2 cm–0.4 cm; Width: <0.1 cm–0.1 cm.
*Diameter of disc.*—0.6 cm–0.9 cm.

Fragrance: Slight.

Flower bud (at onset of color):
*Length.*—0.6 cm–0.8 cm.
*Diameter.*—0.6 cm–0.8 cm.
*Form/shape.*—Ball shaped.

General flower color:
1. *Ray florets, upper side.*—Immature: near 55A. Mature: near 55C. Older/Fading: near 55D.
2. *Ray florets, under side.*—Immature: near 55A. Mature: near 55C. Older/Fading: near 55D.
3. *Disc florets.*—Immature: near 14B. Mature: near 14C. Older/Fading: near 14C.
4. *Bud.*—Near 139C.

Flower progression with age; Flowers fade uniformly with age.

The lastingness of bloom is about 25 days.

Reproductive Organs

Gynoecium present on Ray and Disc florets.

Ray florets per individual flower:
*Pistil number.*—20–25 observed.
*Stigma color.*—Near 144D.
*Stigma shape.*—Forked.
*Style color.*—Near 144D.
*Style length.*—0.1 cm–0.2 cm.

Disc florets per individual flower:
*Pistil number.*—125–140.
*Stigma color.*—Near 144D.
*Stigma shape.*—Forked.
*Style color.*—Near 144D.
*Style length.*—0.1 cm–0.2 cm.

Androecium present on Disc florets only.

Disc florets per individual flower:
*Stamen number.*—70–90 observed.
*Anther shape.*—Clubbed.
*Anther color.*—Near 14C.
*Pollen color.*—Near 12A.
*Pollen quantity.*—Medium.

Fruit and seeds: None observed.

What is claimed is:

1. A new and distinct variety of *Chrysanthemum* plant, substantially as described and illustrated herein.

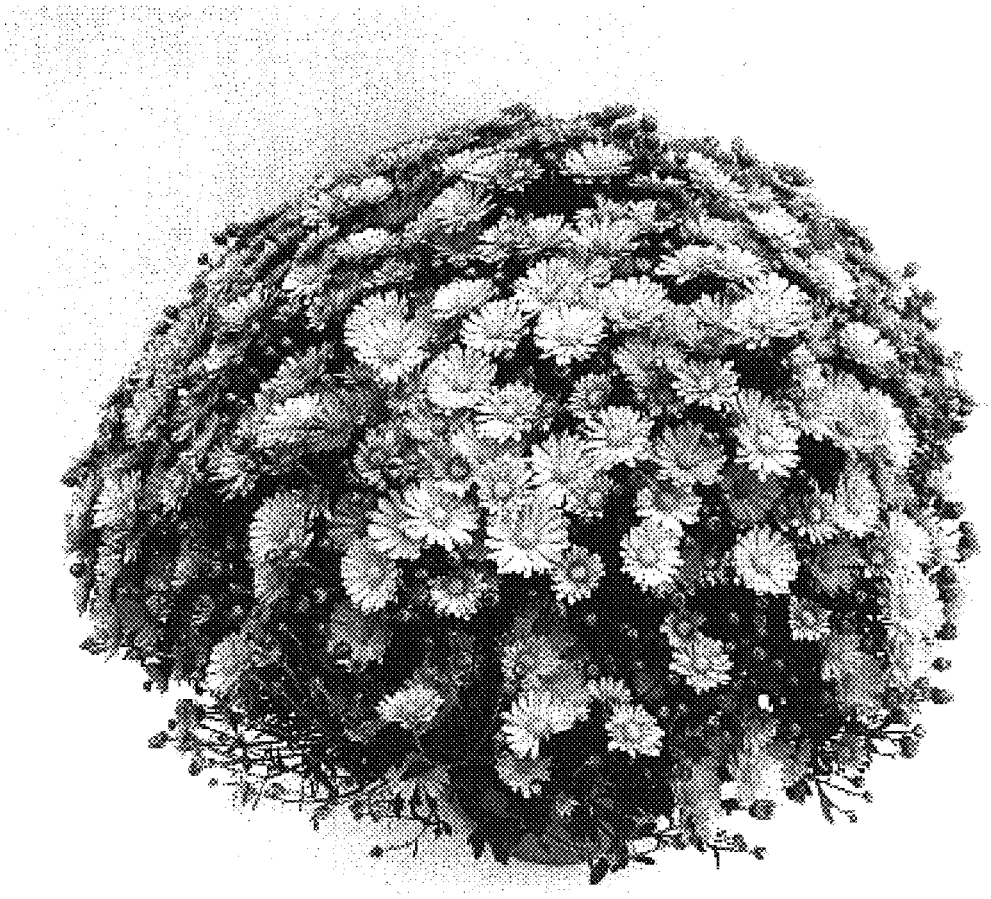

* * * * *